United States Patent
Reynolds

(10) Patent No.: US 8,071,610 B2
(45) Date of Patent: Dec. 6, 2011

(54) COMPOSITIONS AND METHODS FOR ENHANCING BRAIN FUNCTION

(76) Inventor: Josh Reynolds, Laguna Beach, CA (US)

( * ) Notice: Subject to any disclaimer, the term of this patent is extended or adjusted under 35 U.S.C. 154(b) by 911 days.

(21) Appl. No.: 11/758,151

(22) Filed: Jun. 5, 2007

(65) Prior Publication Data

US 2007/0281010 A1 Dec. 6, 2007

Related U.S. Application Data

(60) Provisional application No. 60/803,943, filed on Jun. 5, 2006, provisional application No. 60/820,201, filed on Jul. 24, 2006.

(51) Int. Cl.
*A01N 43/40* (2006.01)
*A01N 43/42* (2006.01)

(52) U.S. Cl. ........................ 514/277; 514/290

(58) Field of Classification Search .................. 514/277, 514/290
See application file for complete search history.

(56) References Cited

U.S. PATENT DOCUMENTS

| | | | |
|---|---|---|---|
| 4,775,536 A * | 10/1988 | Patell | ............................ 424/471 |
| 4,812,447 A | 3/1989 | Roberts | |
| 5,104,880 A | 4/1992 | Kozikowski | |
| 5,221,668 A | 6/1993 | Henningfield et al. | |
| 5,668,117 A | 9/1997 | Shapiro | |
| 5,716,614 A | 2/1998 | Katz et al. | |
| 5,977,162 A | 11/1999 | Seidman | |
| 6,020,139 A | 2/2000 | Schwartz et al. | |
| 6,063,820 A | 5/2000 | Cavazza | |
| 6,117,872 A | 9/2000 | Maxwell et al. | |
| 6,335,361 B1 | 1/2002 | Hamilton | |
| 6,479,069 B1 | 11/2002 | Hamilton | |
| 6,562,869 B1 | 5/2003 | Hamilton | |
| 6,964,969 B2 | 11/2005 | McCleary | |
| 7,030,154 B2 | 4/2006 | Ames | |
| 2005/0053904 A1 | 3/2005 | Shepard | |
| 2006/0014773 A1 | 1/2006 | McCleary | |
| 2006/0211721 A1 * | 9/2006 | Roberts | ........................ 514/276 |

FOREIGN PATENT DOCUMENTS

WO 99/51097 10/1999

OTHER PUBLICATIONS (Tory M. Hagen et al.), Feeding Acetyl-L-Caritine and Lipoic Acid to Old Rats Significantly Improved Metabolic Function While Decreasing Oxidative Stress, Feb. 19, 2002.

* cited by examiner

*Primary Examiner* — Sreeni Padmanabhan
*Assistant Examiner* — Renee Claytor
(74) *Attorney, Agent, or Firm* — Fish & Associates, PC

(57) ABSTRACT

Compositions and methods are provided that enhance cognition in a human to which the composition is orally administered. Remarkably, clinical studies have proven that contemplated compositions achieve the desired effects using a minimal number of active ingredients at or near threshold active dosages, wherein such compositions almost exclusively comprise huperzine A, vinpocetine, and acetyl-L-carnitine at typically less than 1600 mg per daily dosage.

9 Claims, No Drawings

COMPOSITIONS AND METHODS FOR ENHANCING BRAIN FUNCTION

This application claims priority to our U.S. provisional applications with the Ser. Nos. 60/803,943, filed Jun. 5, 2006, and 60/820,201, filed Jul. 24, 2006.

FIELD OF THE INVENTION

The field of the invention is nutritional supplements and methods therefore, especially as they relate to enhancers of cognition and mood.

BACKGROUND OF THE INVENTION

There are numerous approaches known in the art to enhance mood and cognitive performance in normal individuals, including pharmaceutical interventions, aerobic exercise and certain cognitive training programs. Recently, certain nutraceutical agents, such as, ginkgo biloba, and multi-agent compounds have claimed cognitive enhancing effects. Unfortunately, most of those agents and compounds make claims based on mere inclusion of one or more individual ingredients whose clinically demonstrated efficacy level(s), or minimal therapeutic threshold amount(s), are typically not achieved in the proposed multi-agent compound.

In other examples, various supplements and formulations comprising a multiplicity of allegedly active ingredients are marketed as nootropics, or cognitive enhancing agents. For example, the commercially available "Focus Factor" formulation sports over 30 ingredients, while the commercially available "Brain Lightning" formulation has nearly 20 ingredients. Most typically, such formulations are marketed as including multiple active ingredients with respective specific effects, and therefore often suggest that multiple active ingredients will provide additive, or even synergistic beneficial effects. Unfortunately, there is no clinical trial for such formulations that affirms such suggested results. Indeed, the beneficial effects of selected ingredients, which individually show cognitive benefits, but when combined may possibly even be canceled out by sensory or metabolic over-stimulation.

Moreover, the few isolated compounds claiming one or more cognitive effects that have been subjected to well controlled (e.g., randomized, double blind, placebo controlled) clinical trials in relatively significant sample sizes (e.g., >50) have only shown clinical effect in selected populations (e.g., an older population, cognitively impaired, abnormal, or low normal sub-population), and may therefore have no significant effect in a healthy population of relatively wide age range. For example, certain conditions of compromised cognitive and mood function (e.g., chronic stress, sleep loss, depression, poor diet, aging) can be individually treated by targeting and addressing the underlying neuro-chemical imbalance(s). For instance, a lack of certain B vitamins, such as, B-1 or B-12, or minerals, such as, magnesium or selenium, can induce low normal to impaired states of cognition. Such nutritional supplementation can often restore partial or full cognitive functioning. In one example, Oakland intercity kids with extremely low IQ status, were given a cocktail of certain vitamins and minerals and showed an increase of over 10% in IQ points. In general, however, there have been few if any qualified studies showing single or multi-agent compounds positively and significantly effecting mood and cognitive status in a healthy, broad age range population.

Therefore, while numerous compositions and methods for cognitive enhancement are known in the art, all or almost all of them suffer from one or more disadvantages. Thus, there is still a need to provide improved nootropic compositions and methods, for improvements in mood and cognitive function in both abnormal, low normal and normal high functioning general population groups.

SUMMARY OF THE INVENTION

The present invention is directed to compositions and methods of enhancing cognitive function in human, and particularly to orally administered compositions. Especially preferred compositions have been clinically proven to increase selected aspects of mood and cognition and comprise a minimum number of active ingredients near, at or above their proven therapeutic threshold.

In one aspect of the inventive subject matter, a nutritional supplement for enhancing cognitive function includes huperzine A, vinpocetine, and acetyl-L-carnitine in a ratio of x:y:z, wherein x is between 0.8 and 1.2, y is between 80 and 120, and z is between 8,000 and 12,000. Such compositions may further include an optional additional ingredient. Most preferably, the supplement is formulated for oral administration such that the huperzine A, vinpocetine, and acetyl-L-carnitine together account for at least 80 wt % of a dosage unit of the supplement.

Consequently, methods of assisting enhancement of cognitive function in a person using a nutritional supplement are also contemplated in which a composition is provided that includes huperzine A, vinpocetine, and acetyl-L-carnitine in a ratio of x:y:z, wherein x is between 0.8 and 1.2, y is between 80 and 120, and z is between 8,000 and 12,000, and that further may include an optional additional ingredient. The supplement is most preferably formulated for oral administration such that the huperzine A, vinpocetine, and acetyl-L-carnitine together account for at least 80 wt % of a dosage unit of the supplement, and an information is provided that states that the supplement was proven effective in a clinical trial to improve mood and cognitive function.

In especially preferred aspects of the inventive subject matter, x is between 0.9 and 1.1, y is between 90 and 110, and z is between 9,000 and 11,000, and/or at least one of (a) huperzine A is present in the first component an amount of about 150 mcg, (b) vinpocetine is present in the first component an amount of about 15 mg, and (c) acetyl-L-carnitine is present in the first component an amount of about 1,500 mg. Where desired, the optional additional ingredient is folic acid in an amount of at least 1 mg per dosage unit or potassium in an amount of at least 100 mg per dosage unit, and/or the additional ingredient is an inactive ingredient selected from the group consisting of a carrier, a binder, an excipient, and a dye. Moreover, the supplement may also be formulated with an enteric coating.

Additionally, it is generally preferred that the huperzine A, vinpocetine, and acetyl-L-carnitine together account for at least 90 wt % (or even at least 95 wt %) of a dosage unit of the supplement, and that the dosage unit of the supplement is equal or less than 1,600 mg. In further contemplated aspects, an information may be associated with the supplement stating that the nutritional supplement enhances at least one of short term working memory, memory consolidation and processing speed, mental clarity, mental energy, fluid intelligence, general reasoning and mood, and where desirable, an interactive tool may be provided that allows at least one of validation of efficacy of the supplement and proper personal dosing, or titration of the supplement.

Various objects, features, aspects and advantages of the present invention will become more apparent from the following detailed description of preferred embodiments of the invention.

DETAILED DESCRIPTION

The inventor has discovered that specific combinations of nutritionally safe compounds have significant and desirable effect on cognitive and mood function while having a minimum number of active ingredients at proven minimal therapeutic threshold levels. Moreover, all of the active ingredients in contemplated compositions were selected to impact the largest number of neuro-cognitive structures and functions in the human brain. Furthermore, contemplated compositions are effective for optimal improvement of cognitive states and status ranging from normal to declining more rapidly than normal, or accelerated stages of decline, to pre-dementia states (e.g., MCI—mild cognitive impairment), and even MCI precursor states (e.g., AAMI).

It should be particularly appreciated that contemplated formulations are, to the best of the inventor's knowledge, the first formulations that have been administered to a cognitively normal, or healthy, broad age range group and clinically shown to enhance short term working memory, memory consolidation and processing speed, mental clarity and energy, fluid intelligence, general reasoning and a broad range of moods (e.g., to reduce depressed states, anxiety, confusion, hostility and anger). Particularly, contemplated compositions have been demonstrated to improve with high statistical significance numerical working memory accuracy (working memory), word recognition speed (long term memory consolidation), anger-hostility (mood), total mood disturbance (mood), and the Raven Progressive Matrices test of fluid intelligence, visual-spatial and object working memory, and general reasoning. Contemplated compositions have further substantially improved (to near statistical significance) spatial working memory accuracy (working memory), depression (mood), confusion (mood), and vigor (mood).

In contrast, heretofore known nootropic formulations include a large range of ingredients (e.g., U.S. Pat. No. 6,964,969 listing 47 ingredients) with unknown interactions, wherein clinical information on cognitive enhancement was only available for isolated ingredients. Therefore, and as pointed out in more detail further below, the presumed effect of such formulations was based on a summarization of known effects of individual ingredients, which is in most if not all cases inconsistent with the actual effect. On the other hand, certain supplements have been tested and were found effective in a specific manner (e.g., Eur. J. Pharmacol. 2000; 398 (1):56-72 where improvement of cognitive function in rats with chronic cerebral hyperfusion is reported). As a consequence, these supplements are often marketed with unsubstantiated and/or overextended claims with regard to their alleged effect on human cognition as the reported and specific effects often fail to translate into specific and measured advantages in human.

In one exemplary and preferred formulation, a nutritional supplement or pharmaceutical composition is prepared that includes a therapeutically effective daily dosage of (1) acetyl-L-carnitine (preferably 1250-2000 mg/d, and even more preferably 1500 mg/d), (2) Vinpocetine (preferably 10-30 mg/d, and even more preferably 15 mg/d), and (3) Huperzine A (preferably 50-200 mcg/d, and even more preferably 150 mcg/d). Most preferably, the effective daily dosage is administered between once daily and four times daily in dosage units of accordingly adjusted weight. While not limiting to the inventive subject matter, acetyl-L-carnitine in contemplated formulations is thought to increase cerebral energy metabolism by assisting in mitochondrial beta-oxidation and to donate an acetyl moiety for synthesis of acetylcholine, while Vinpocetine is thought to dilate blood vessels in the brain, as well as improve red blood cell deformability, to thus allow for better perfusion into and throughout neuro-cognitive regions and structures of the brain. Huperzine A is thought to act as an acetylcholine esterase inhibitor and antioxidant.

Therefore, and viewed from a different perspective, contemplated nutritional supplements for enhancing cognitive function include huperzine A, vinpocetine, and acetyl-L-carnitine in a ratio of x:y:z, wherein x is between 0.8 and 1.2 (and more preferably between 0.9 and 1.1), y is between 80 and 120 (and more preferably between 90 and 110), and z is between 8,000 and 12,000 (and more preferably between 9,000 and 11,000). Such supplements may also further comprise an additional ingredient, wherein the supplement is formulated for oral administration such that the huperzine A, vinpocetine, and acetyl-L-carnitine together account for at least 80 wt %, more preferably at least 90 wt %, and most preferably at least 95 wt % of a dosage unit of the supplement. Therefore, huperzine A is typically present in the first component an amount of about 150 mcg, vinpocetine is present in the first component an amount of about 15 mg, and/or acetyl-L-carnitine is present in the first component an amount of about 1,500 mg. As used herein, the term "about" in conjunction with a numeral refers to a range of that numeral +/−10%, inclusive.

Where desired, optional additional active ingredients may be added, and especially contemplated include folic acid (typically in an amount of at least 0.1 mg per dosage unit, and more preferably at least 1 mg per dosage unit) or potassium (typically in an amount of at least 10 mg per dosage unit, and more preferably at least 100 mg per dosage unit). Furthermore, contemplated supplements may include inactive ingredients, which may help in formulation, disintegration, or other manner. Therefore, suitable inactive ingredients include carriers, binders, excipients, dyes, etc. Oral formulation is typically in form of a liquid or powder, or gel, or a solid form, and most preferably in form of tablet, pill, dragee, capsule, or softgel which may or may not have an enteric coating, such coating allowing for the ingredients to by-pass the upper GI tract where gastro-intestinal disturbances can be problematic for some individuals. Moreover, one or more of the active ingredients may be in slow release formulation to extend release over a period of between 1-24 hours. In less preferred aspects, the supplement may also be formulated as a liquid or a gel, or embedded in a dissolvable film or chewing preparation.

It is further preferred that the supplement is formulated such that the daily dosage unit of the supplement is equal or less than 1,800 mg, and more preferably equal or less 1,600 mg, wherein administration may be between once daily and ten times daily. Therefore, suitable oral single dosage forms may preferably have a weight between 200 mg and 600 mg. Regardless of the actual weight of the single dosage form, it is preferred that the huperzine A, vinpocetine, and acetyl-L-carnitine together account for at least 85 wt %, more typically at least 90 wt %, and most typically at least 95 wt % of the dosage unit of the supplement.

With respect to marketing such compositions it is contemplated that the supplement may be associated with an information (e.g., printed, displayed, or audio) stating that the nutritional supplement enhances short term working memory, memory recall capacity and memory recall speed, mental clarity, mental energy, fluid intelligence, and/or mood. Most preferably, such statement is included on a packaging label. Furthermore, contemplated supplements may be provided with an interactive tool (e.g., computer software, link, flash cards, electronic device, etc.) that allows for testing, training, and/or validation of the cognitive enhancement or that allows for validation of efficacy of the supplement and/or proper personal dosing, or titration of the supplement to achieve optimal efficacy.

Consequently, a method of assisting enhancement of cognitive function in a person using a nutritional supplement includes a step of providing a composition that includes huperzine A, vinpocetine, and acetyl-L-carnitine in a ratio of x:y:z, wherein x is between 0.8 and 1.2, y is between 80 and 120, and z is between 8,000 and 12,000, and further providing an optional additional ingredient; formulating the supplement for oral administration such that the huperzine A, vinpocetine, and acetyl-L-carnitine together account for at least 80 wt % of a dosage unit of the supplement; and providing an information that the supplement in a clinical trial was effective to improve cognitive function (with respect to the composition of the supplement, the same considerations as described above apply). Most typically, the cognitive function is a function of working memory, a function of memory processing speed and consolidation, an aspect of mood, a function of fluid intelligence, spatial memory, semantic memory, object working memory and general reasoning. As already pointed out above, the supplement may be provided with an interactive tool that allows at least one of validation of efficacy of the supplement and proper personal dosing, or titration of the supplement.

EXPERIMENTS

Clinical Study Results of Inventive Composition Vs. Comparative Composition

In the following, the composition according to the inventive subject matter is referred to as Procera, while the second composition was termed comparative composition. Most notably, Procera produced significant widespread, global cognitive effects in short term memory, working memory, and longer term memory consolidation and sped of processing speed measures. Furthermore, Procera produced significant or near significant improvement in IQ (fluid intelligence; general reasoning, visual problem solving and object working memory as measured by the Ravens Progressive Matrices, a highly standardized Wechsler IQ test that shows the highest predictive validity for social mobility, occupational ranking and job level and potential). What's more, test subjects displayed improvement in a range of mood measures including depression, anxiety, anger and hostility, and exhibited more mental vigor, confidence and clarity.

It should further be appreciated that the study was conducted with cognitively normal male and female subjects ranging in age form 25-60. Producing an overall effect in such a large demographic group is unexpected. Rather, it could be expected that the type of formulation used herein would only show significant improvements in either a slightly to moderately impaired group and an older group (e.g., age 45 plus), where many conditions of aging and lifestyle factors contribute to an accumulated buildup of neurotoxic factors (e.g., free radical induced oxidative stress, heavy metals, cerebral vascular plaques, including beta amyloid plaques implicated in Alzheimer's, reduced cerebral vascular blood flow and glucose metabolism, calcium dyshomeostasis and others).

| Procera Composition (daily dose in mg) | |
|---|---|
| Huperzine A | 0.15 |
| Vinpocetine | 15 |
| Acetyl-L-Carnitine | 1500 |

| Comparative Composition (daily dose in mg) | |
|---|---|
| Huperzine A | 0.15 |
| Vinpocetine | 20 |
| Acetyl-L-Carnitine | 1000 |
| Pantothenic Acid | 250 |
| DMAE | 300 |
| Thiamin | 100 |
| Niacin (niacinamide) powder | 250 |

As can be seen, the comparative composition employs similar but significantly distinct amounts of huperzine A, vinpocetine, and acetyl-L-carnitine, and further includes four active ingredients known to have certain cognitive effects as isolated compounds, and purported to act synergistically with the cholinergic-enhancing effects of acetyl-1-carnitine and Huperzine A.

Methods

Participant Selection Criteria; Selection criteria includes those: (1) Not currently taking prescription drugs affecting the brain or nervous system (e.g., Modafinil, acetylcholinesterase inhibitors, anti-cholinergics, stimulants, L-dopa, MAO inhibitors, NMDA receptor antagonists, methylphenidate, amphetamine, pseudo-ephedrine, SSRIs and other anti-depressant medication);

(2) Not currently taking OTC medications affecting the brain (e.g., ephedra based diet pills); (3) Who have not used any supplements within the past 30 days that have an effect on cognitive function, memory, anxiety, depression (e.g. Ginseng, Gingko, Vinpocetine, 5HTP, Tryptophan, St. John's Wort, ephedrine (ephedra), alpha GPC, Citicoline, phosphatidylserine, acetyl-1-carnitine, Focus Factor™); (4) Not active Smokers; (5) Not taking the following: anticoagulant drugs (Warfarin, Heparin, Plavix); anticholinergics or acetylcholinesterase inhibitors (bethanechol (Ureholine), donepezil (Aricept), rivastigmine (Exelon), galantamine (Reminyl), edrophonium (Enoln, Reversol, Tensilon), neostigmine (Prostigmin); (6) Do not have any of the following health conditions: AIDS, HIV; Chronic Fatigue Syndrome, Epstein Barr, Fibromylagia, Lupis, Multiple Sclerosis, Thyroiditis, Ulcerative Colitis, Crohn's Disease, Irritable Bowel Syndrome, dementia including Alzheimer's and Parkinsons' disease, Type 1 or 2 Diabetes, Insomnia or Sleep Apnea, Narcolepsy; (7) No history of head trauma; (8) No neurological deficits; (9) Not pregnant or lactating; (10) Not anticipating any planned changes in lifestyle (e.g. exercise regimen) for the duration of the study; (11) No known allergies to nuts.

Fifty healthy participants between the ages of 25-65 years of age, were tested in treatment and placebo groups (total number of participants is n=100). A drop out rate (voluntary and non-voluntary withdrawal) of approximately 20% was expected and therefore additional participants were recruited for the study. The study was advertised in Melbourne newspapers, on community notice boards, the Brain Sciences Institute website, and via the Brain Sciences Institute database of interested participants. All interested individuals were screened over the phone by the research nurse to assess their suitability for participation in the study. Subjects participated in periodic evaluation of their cognitive functions including memory, mood, energy and mental status by taking a battery of computerized tests and written questionnaires that assessed their cognitive functions which including attention, memory, executive function, mood, energy, stress level, state of mind and IQ.

The following neuropsychological tests were employed in the currents study:

(1) The Cognitive Drug Research measure (CDR) is a well-validated test, which was used to assess attention, working memory and episodic secondary (longer term memory, or consolidation). (2) Inspection time (IT) is a measure speed of early information processing. (3) The Profile of Mood States (POMS) is a self-report designed to measure six dimensions of mood: tension-anxiety; depression-dejection; anger-hostility; vigor-activity; fatigue-inertia; and confusion-bewilderment. (4) IQ was assessed using the Raven's Progressive Matrices. This was done by administering the even items at baseline and the odd items at Week 4. (5) The UWIST Mood Adjective Checklist was used to measure mood states and energy levels. (6) The Spielberger State-Trait Anxiety Inventory is a 20-item questionnaire, to measure anxiety at the time of testing. (7) Perceived Stress Scale was used to measure stress symptoms and effective coping.

Participants visited Swinburne University on 3 separate occasions 1) Visit 1: Health assessment, practice, baseline and acute testing 2) Visit 2: 1 week (7 days) following baseline testing and 3) Visit 3: 4 weeks (28 days) following baseline testing. During the first visit, participants completed a general health assessment and were then allocated into one of three treatment groups for baseline and acute testing. Timeline for each testing period:

Baseline and Acute Testing

Baseline testing: 1. General health assessment: blood pressure, height, weight; 2. Random allocation of participants into one of the three treatment groups; 3. CDR practice testing which is required in order to become familiar with the tests and what is required of participants; 4. CDR baseline testing; 5. Mood and energy scales will be administered—POMS, STAI, UWIST mood adjective checklist, PSS and Raven's Matrix Acute testing: 6. Groups were administered an initial dose of 2 tablets along with a snack of a peanut butter sandwich for adequate absorption of fat-soluble ingredients and minimization of gastric distress from the consumption of acetyl-1-carnitine. 7. 30 mins. after initial dose of 2 tablets, a second dose of 2 tablets was administered again with a snack as in step 5. 8. Following 60 minutes after the second dose (90 minutes after initial dose) participants performed CDR testing. Participants were then asked to take the appropriate number of tablets per day for 4 weeks (28 days) according to their assigned treatment group. All participants were asked to visit Swinburne University for a re-test at week 1 and at the completion of the treatment period at week 4. Subjects were given a Symptom Checklist to take home to monitor for any side effects and symptoms that they experience on a weekly basis.

Testing sessions 2 and 3 (1 and 4 weeks following baseline testing; Total time=approx 50 minutes): 1. CDR, Inspection Time and Raven's matrix (week 4 only). 2. Mood and energy scales will be administered—POMS, STAI, UWIST mood. Adjective checklist, PSS; 3. Participants submitted weekly symptom checklist 4. General health assessment.

We used alternate forms of psychometric tests to reduce practice effects as much as possible and to maximize the power of the study. General health assessments were undertaken by the BSI research nurse. Testing sessions were consistent on each testing day. Participants were requested not to have alcohol or caffeine-containing food or beverages on the testing days (e.g., coffee, tea, chocolate and energy drinks containing caffeine or guarana). Further to control for food intake participants they were also required to eat a light breakfast (e.g., 2 pieces of toast or cereal with juice) on the testing days.

Results

Cognitive Measures

Simple Reaction Time: The speed of simple reaction time did not significantly improve due to the Procera treatment across the 4 weeks of administration. This is the simplest cognitive measure in the cognitive battery.

Digit Vigilance and Choice Reaction Time: These measures were excluded from analysis because of the large number of participants who reached 100% accuracy at baseline serving to cause these variables to show a ceiling effect. This effect significantly reduces the variance in measures and invalidates parametric (statistical) testing of differences. Conceptually it is pointless to examine an effect of improvement from baseline to time two if the majority of the sample has already reached perfect performance at baseline.

Spatial Working Memory: There was a trend towards significance for Spatial Working Memory Accuracy (p=0.17). Although not significant, the results (see mean values below) indicate that there was more of an improvement in accuracy over the treatment duration for the Procera than for the placebo. Larger sample size may help this result become statistically significant. This result should be treated as a preliminary finding that should be subjected to replication in a larger sample.

|  | Condition | Mean | Std. Deviation | N |
|---|---|---|---|---|
| Spatial Working Memory New Stimuli - Accuracy - baseline | Procera AVH | 94.7222 | 8.53099 | 36 |
|  | Placebo | 96.6071 | 5.27987 | 28 |
|  | Total | 95.5469 | 7.29847 | 64 |
| Spatial Working Memory New Stimuli - Accuracy - Week 4 |  | 97.0833 | 5.52591 | 36 |
|  | Placebo | 97.1429 | 5.51573 | 28 |
|  | Total | 97.1094 | 5.47757 | 64 |

There was also a trend towards statistical significance (p=0.09) for the number of outliers during the spatial working memory task. Outliers indicate lapses in concentration over the duration of the task. As can be seen in the table below, participants in the Procera treatment group showed less mean number of such lapses during the task and were therefore better able to focus and concentrate/process during the spatial working memory task which is a complex cognitive task.

| | Condition | Mean | Std. Deviation | N |
|---|---|---|---|---|
| Spatial Working Memory - Outliers - baseline | Procera AVH | 1.0256 | 1.03840 | 39 |
| | Placebo | .7813 | .83219 | 32 |
| | Total | .9155 | .95239 | 71 |
| Spatial Working Memory - Outliers - week 4 | Procera AVH | .7179 | 1.02466 | 39 |
| | Placebo | .9063 | 1.20106 | 32 |
| | Total | .8028 | 1.10350 | 71 |

Numerical Working Memory: Participants on the Procera treatment showed statistically significant improvement (p=0.03) in Numerical Working Memory Accuracy compared to placebo participants. A statistically significant improvement in holding numbers in working memory (immediate memory) was shown from Baseline to Week four due to the Procera treatment.

| | Condition | Mean | Std. Deviation | N |
|---|---|---|---|---|
| Numeric Working Memory Original Stimuli - Accuracy - baseline | Procera AVH | 93.7653 | 5.14656 | 36 |
| | Placebo | 95.7787 | 5.26386 | 30 |
| | Total | 94.6805 | 5.25784 | 66 |
| Numeric Working Memory Original Stimuli - Accuracy - week 4 | Procera AVH | 95.4333 | 3.39970 | 36 |
| | Placebo | 95.0380 | 3.94556 | 30 |
| | Total | 95.2536 | 3.63433 | 66 |

Picture Recognition: There was no significant change in performance in Picture Recognition over the 4 week trial attributable to either Placebo or Procera treatment.

Word Recognition: Word Recognition Accuracy improved for the Procera participant group but decreased for the Placebo participant group across the 4 weeks of the trial. Although this approached statistical significance (p=0.12) this results suggests that Procera improves the accuracy of memory consolidation of words.

| | Condition | Mean | Std. Deviation | N |
|---|---|---|---|---|
| Word Recognition Original Stimuli - Accuracy - baseline | Procera AVH | 73.3336 | 16.25226 | 36 |
| | Placebo | 74.2534 | 14.87757 | 29 |
| | Total | 73.7440 | 15.54023 | 65 |
| Word Recognition Original Stimuli - Accuracy - week 4 | Procera AVH | 75.1853 | 15.50148 | 36 |
| | Placebo | 73.1038 | 14.19566 | 29 |
| | Total | 74.2566 | 14.85472 | 65 |

Word Recognition: The speed of performance during the Word Recognition task was significantly improved (p=0.02) for participants on the Procera treatment compared to the placebo treatment over the 4 weeks of administration. This indicated that Procera significantly improved memory consolidation processes and in particular the speed at which a participant was able to consolidate and access new memories into long term storage.

| | Condition | Mean | Std. Deviation | N |
|---|---|---|---|---|
| Word Recognition Original Stimuli - Speed: Mean - baseline | Procera AVH | 853.1267 | 184.99467 | 36 |
| | Placebo | 774.9913 | 122.44679 | 30 |
| | Total | 817.6106 | 163.26059 | 66 |
| Word Recognition Original Stimuli - Speed: Mean - week 4 | Procera AVH | 757.5228 | 138.40862 | 36 |
| | Placebo | 750.5463 | 147.03377 | 30 |
| | Total | 754.3517 | 141.32551 | 66 |

Inspection Time: A small sub set of participants completed this task. No differences were observed between the Procera and placebo groups but this may be due to the low sample size.

Raven Progressive Matrices: Participants in the Procera group scored statistically higher (p=0.02) on the Raven Progressive Matrices at the end of the 4 week trial than did placebo participants, The Placebo and Procera group were not statistically different at baseline suggesting that 4 week administration of Procera improves general reasoning, visual problem solving and object working memory. This result supports the improvement in spatial and numerical working memory shown in the trial.

| | Condition | N | Mean | Std. Deviation | Std. Error Mean |
|---|---|---|---|---|---|
| Raven's - advance progressive matrix - baseline | Procera AV | 30 | 11.1000 | 2.57776 | .47063 |
| | Placebo | 22 | 10.5000 | 2.54015 | .54156 |
| Raven's - advance progressive matrix - w 4 | Procera AV | 30 | 11.2667 | 3.24763 | .59293 |
| | Placebo | 24 | 9.4167 | 3.38689 | .69135 |
| Raven's - advance progressive matrix - T | Procera AV | 33 | 21.3030 | 5.74176 | .99951 |
| | Placebo | 26 | 18.4615 | 6.09413 | 1.19516 |

It should be noted that the Raven Progressive Matrices Set that was administered to both groups at 4 weeks was significantly harder than the set administered to the two groups at baseline.

Mood Measures Depression (p=0.06): The Procera group showed a decrease in depression scores relative to the placebo group. This suggests that Procera may improve depressive mood.

|  | Treatment | Mean | Std. Deviation | N |
|---|---|---|---|---|
| depression dejection baseline (POMS) | Procera AVH | 8.0000 | 9.42388 | 43 |
|  | Placebo | 5.1935 | 8.54174 | 31 |
|  | Total | 6.8243 | 9.11172 | 74 |
| depression dejection Week 4 (POMS) | Procera AVH | 4.3256 | 5.12566 | 43 |
|  | Placebo | 4.3548 | 6.57038 | 31 |
|  | Total | 4.3378 | 5.73209 | 74 |

Vigor (p=0.10): The Procera group showed an improvement in Vigor over the 4 weeks of the trial relative to the placebo group.

|  | Treatment | Mean | Std. Deviation | N |
|---|---|---|---|---|
| vigor baseline (POMS) | Procera AVH | 18.140 | 5.4711 | 43 |
|  | Placebo | 17.581 | 6.5359 | 31 |
|  | Total | 17.905 | 5.9037 | 74 |
| vigor Week 4 (POMS) | Procera AVH | 19.5116 | 6.38589 | 43 |
|  | Placebo | 17.2903 | 6.72901 | 31 |
|  | Total | 18.5811 | 6.57935 | 74 |

Anger Hostility (P<0.03): The Procera group showed a statistically significant decrease in anger-hostility over the 4 week trial relative to the placebo group. This indicates that 4 week treatment with Procera significantly improves feelings of anger and hostility. This result is supportive of the decrease in depression scores.

|  | Treatment | Mean | Std. Deviation | N |
|---|---|---|---|---|
| anger hostility baseline (POMS) | Procera AVH | 7.8372 | 7.56222 | 43 |
|  | Placebo | 4.4839 | 5.80730 | 31 |
|  | Total | 6.4324 | 7.03821 | 74 |
| anger hostility Week 4 (POMS) | Procera AVH | 4.1628 | 4.30907 | 43 |
|  | Placebo | 3.8065 | 6.12329 | 31 |
|  | Total | 4.0135 | 5.11108 | 74 |

Confusion (p=0.06): Participants in the Procera group also showed a decrease in confusion over the 4 week trial which was greater than the placebo participants. Again this result is consistent with the decrease in depression and anger hostility shown by the Procera participants over the 4 week trial.

|  | Treatment | Mean | Std. Deviation | N |
|---|---|---|---|---|
| confusion baseline (POMS) | Procera AVH | 8.9302 | 4.74791 | 43 |
|  | Placebo | 7.5806 | 3.42320 | 31 |
|  | Total | 8.3649 | 4.27024 | 74 |
| confusion Week 4 (POMS) | Procera AVH | 6.1628 | 3.01528 | 43 |
|  | Placebo | 6.5161 | 3.94859 | 31 |
|  | Total | 6.3108 | 3.41602 | 74 |

Total Mood Disturbance (p=0.02): Participants in the Procera group showed a highly statistically significant reduction in mood disturbance over the 4 week duration of the trial relative to the placebo participants. This result indicates that 4 week Procera treatment is highly beneficial for improving mood.

|  | Treatment | Mean | Std. Deviation | N |
|---|---|---|---|---|
| Total mood disturbance score BL (POMS) | Procera AVH | 65.9302 | 30.50870 | 43 |
|  | Placebo | 52.9032 | 23.86120 | 31 |
|  | Total | 60.4730 | 28.48466 | 74 |
| Total mood disturbance score Week 4 (POMS) | Procera AVH | 47.5581 | 17.16905 | 43 |
|  | Placebo | 46.5161 | 26.53158 | 31 |
|  | Total | 47.1216 | 21.42777 | 74 |

Procera Study Summary

The results of this study clearly indicate that contemplated formulations of Huperzine, Vinpocetine, and Acetyl-L-Carnitine improve both cognition and mood in healthy participants aged 25-60 years. Statistically significant improvements in several variables relative to placebo could be attributed to the 4 week administration of Procera, and particularly Numerical Working Memory Accuracy (working memory), Word Recognition Speed (long term memory consolidation), Anger-Hostility (mood), Total Mood Disturbance (mood), and Raven Progressive Matrices (fluid intelligence, general reasoning and spatial and object working memory). Placebo was a sugar pill.

The study also found some evidence approaching statistical significance of the following measures to be improved due to the 4 week Procera treatment: Spatial Working Memory Accuracy (working memory), Depression (mood), Confusion (mood), and Vigor (mood).

Alternative Formulation Summary

Remarkably, cognition and mood in healthy participants was not improved in statistically significant manner or even in a manner approaching statistical significance. Study design for this formulation was substantially as outlined below under the section "Additional Comparative Examples".

It should be noted that the overall compositions and respective amounts of ingredients of the comparative composition and contemplated compositions were relatively similar, but did produce significantly different results. Indeed, while the comparative composition failed to provide any measurable advantage (no significant effects on mood, mental clarity or memory, either working memory or longer term memory consolidation or processing speed), or IQ (fluid intelligence), contemplated compositions were statistically significant in a controlled clinical trial. This is especially unexpected as DMAE and selected B vitamins of the comparative composition were thought to be important contributors to and co-factors for a cholinergic enhancement effects of the acetyl-l-carnitine and Huperzine A.

Without wishing to be bound by any theory or hypothesis, it is contemplated that various factors may have contributed to the above difference. For example, the comparative composition may over stimulate neuro-cognitive brain cell receptors, in effect undermining cognitive function and behavior (e.g., mood). This is often seen with pharmaceutical agents that over stimulate brain cells, thus down regulating receptor sensitivity and/or density in the corresponding neurotransmitter system, or neuro-cognitive brain area. Downregulation in any neurotransmitter system can cause swift and ultimately debilitating declines in cognitive and/or psychological (mental health) functions, e.g., memory and mood, respectively.

Moreover, the additional ingredients, even though promising on paper, somehow reduce neural-cognitive function and/or attenuate or cancel the Procera effect of the comparative composition. In this context, it should be noted that there are many putative cognitive enhancers on the market that claim clinical proof based on presence of multiple active ingredients. Such enhancers will likely suffer from the same drawback as the comparative composition, or have the active ingredients in minute quantities present that will not have any perceivable effect.

Additional Comparative Examples

Chronometric (brain speed) testing can identify what information processing stage is impacted by the therapeutic agent. This may include: motor reflexes (physical reaction time); perceptual acuity; executive function (decision-making speed) and attention; alertness; mental agility (fluid intelligence), and memory (immediate & delayed).

The following CogCAM™ tests were used: CogCAM 4 Working Memory Speed (decision-making; task-shifting); CogCAM10A Memory Scanning (semantic; letters); CogCAM 10B Memory Scanning (visual-spatial; symbols); CogCAM 1 physical reflexes (simple reaction time; attention). These tests provide primary measures of attention, memory and executive cognitive function.

Inclusion Criteria: Male, and non-pregnant (self reported) female subjects, 18 years of age or older, no planned change in lifestyle including exercise regimen during study.

Exclusion Criteria: 1. Taking prescription drugs affecting the brain or nervous system within two weeks of study entry (e.g. epilepsy, Alzheimer's disease, Parkinson's disease, anxiety, depression, psychosis, ADD or other psychiatric condition); 2. Taking OTC medications affecting the brain within two weeks of study entry (e.g. diet pills); 3. Taking supplements known to have an effect on cognitive function, memory, anxiety, depression within two weeks of study entry (e.g. Arctic root or Rhodiloa, Ginseng, Gingko, Vinpocetine, 5HTP, St. John's wort, ephedrine (ephedra), phosphatidyl choline, phosphatidyl serine, alpha GPC, acetyl-l-carnitine); 4. Smokers

| Formulation C | |
|---|---|
| Vinpocetine | 20 mg |
| Pantothenic Acid (Vit. B-5) | 250 mg |
| Dimethylaminoethanol | 300 mg |
| Thiamin (Vit. B-1) | 250 mg |
| Niacin (Vit. B-3) | 20 mg |

| Formulation E | |
|---|---|
| Huperzine A | 150 mcg |
| Vinpocetine | 20 mg |
| Pantothenic Acid (Vit. B-5) | 250 mg |
| Dimethylaminoethanol | 300 mg |
| Thiamin (Vit. B-1) | 250 mg |
| Niacin (Vit. B-3) | 20 mg |
| Acetyl L Carnitine | 1000 mg |

Methods and Results

To assess the influence of multiple formulations of Formulation C and E on cognitive function, a battery of web-based tests (the Cognometer) was administered over a 6-week treatment period. An analysis of the data compared baseline performance to subsequent weekly exams with placebo or 1 of 5 formulations taken daily to determine if there was a change in cognitive function after initiation of treatment with the dietary supplement compounds in cognitively intact individuals 18 to 74 years of age.

Cognitive performance measures were obtained from web-based assessments using the Cognometer test battery subtests; 4-Executive function and 10-Immediate Memory. There were 2 treatment groups and one control group in this study. The group conditions remained blinded in these analyses, the analyses were completed without knowledge of which groups received the test compounds or placebo. Only individuals who completed tests in each of week (e.g., baseline and all dosing weeks) were included in the analysis. Outliers who scored more than two standard deviations from the mean on a test, and were not internally consistent with other test scores were also eliminated. The elimination of outliers was done to avoid including results that may be due to distractions or web/computer glitches that could invalidate the particular test session. Analysis of the data uses an analysis of variance (ANOVA) for the differences between the baseline and last week of treatment.

Results and Statistical Analysis

The current trial used the internet to recruit, qualify, register and test over 1000 subjects with 430 completing the 6 week study. Testing was conducted at week 0, Baseline, and every subsequent testing and reporting week for 6 weeks during which subjects were administered the test compounds. On each test day subjects also completed adverse event forms, questionnaires concerning any changes in lifestyle factors, and cognitive testing.

Following is a description of the Cognometer Tests 4 and 10 used in the testing of the compounds and the interpretative data and possible claims that improvement in these tests represent and support.

Test 4 is a "complex choice reaction time task" that tests so called executive cognitive function, or decision making performance speed measured in milliseconds (ms). It has an added unique feature of a random rule reversing cue which tests both one's ability to rapidly inhibit one mode of response and switch to another response mode, considered a higher order cognitive function. Facility in "inhibition and task shifting" can be equated to mental flexibility. Improvement in reaction time on this test supports the claims of: improved mental quickness and flexibility; improved decision making; improved decision making speed; improved cognitive processing; improved decision making speed in a demanding cognitive task.

Test 4 RT data can also be analyzed to assess the group's level of focus, or attention. This measure is derived from computing the standard deviation of the individual's intra trial reaction times (RTSD). This basically represents the consistency of their responses (processing efficiency) and is considered to reflect the level of sustained attention. Improved performance on this score, that is RTSD, supports claims of: improved attention or focus; improved attention or focus on a demanding cognitive task.

Test 10 is divided into two tests, recognition recall of letters and spatial patterns. Only the visuo-spatial memory part of this test showed significance. This test is patterned after the Sternberg Memory Scan paradigm wherein immediate and short term memory processing (scanning & recall) speed equates to memory encoding. Sternberg-like tests, like Cognometer Test 10, have been used for over 30 years in clinical trials and pharmaceutical research to determine drug effects on memory processes. Improved reaction times on this test support claims of: improved memory; improved memory processing speed; improved encoding of information; improved recall speed.

The most notable, however, statistically insignificant effects were found in the 35 plus age group, probably suggesting that the compounds may be effective in those who are beginning to exhibit normal age related slowing associated with increased years of life, typically after 30 years of age. Reaction time standard deviation (RTSD) for this test of executive function did not show a significant difference between groups. The reaction time median scores (RTmed), a measure of executive function (decision making and mental flexibility) did also not indicate significant between group differences.

Selected results are as follows, with group A taking placebo, group C taking Formulation C, and group E taking Formulation E.

| RT Median - Test 4 | | |
| --- | --- | --- |
| Group | Mean | SEM |
| A | 91.509 | 2.498 |
| C | 88.315 | 2.343 |
| E | 94.505 | 2.352 |

| RT Standard deviation - Test 4 | | |
| --- | --- | --- |
| Group | Mean | SEM |
| A | 85.045 | 5.695 |
| C | 89.4 | 4.588 |
| E | 88.8 | 5.506 |

| RT Median (shapes) - Test 10 | | |
| --- | --- | --- |
| Group | Mean | sem |
| A | 91.523 | 2.016 |
| C | 95.698 | 2.797 |
| E | 93.103 | 2.093 |

Thus, no significant improvement in cognitive functions was observed with those formulations tested. Such finding is once more remarkable as the formulations appear to have similar compositions, but significantly different effects in toto.

Thus, specific embodiments of nutritional supplements for enhancing cognitive function have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Furthermore, where a definition or use of a term in a reference, which is incorporated by reference herein is inconsistent or contrary to the definition of that term provided herein, the definition of that term provided herein applies and the definition of that term in the reference does not apply.

What is claimed is:

1. A method of assisting enhancement of cognitive function in a person using a nutritional supplement, comprising:
   providing a composition that includes huperzine A, vinpocetine, and acetyl-L-carnitine in a ratio of x:y:z, wherein x is between 0.8 and 1.2, y is between 80 and 120, and z is between 8,000 and 12,000, and further providing an optional additional ingredient;
   formulating the supplement for oral administration such that the huperzine A, vinpocetine, and acetyl-L-carnitine together account for at least 80 wt % of a dosage unit of the supplement; and
   obtaining data in a clinical trial that establishes that the quantities and ratios of huperzine A, vinpocetine, and acetyl-L-carnitine in the supplement are effective to improve cognitive function.

2. The method of claim 1 wherein x is between 0.9 and 1.1, y is between 90 and 110, and z is between 9,000 and 11,000.

3. The method of claim 1 wherein at least one of (a) huperzine A is present in the first component an amount of about 150 mcg, (b) vinpocetine is present in the first component an amount of about 15 mg, and (c) acetyl-L-carnitine is present in the first component an amount of about 1,500 mg.

4. The method of claim 1 wherein the supplement is formulated with an enteric coating.

5. The method of claim 1 wherein the additional ingredient is an inactive ingredient selected from the group consisting of a carrier, a binder, an excipient, and a dye.

6. The method of claim 1 wherein the huperzine A, vinpocetine, and acetyl-L-carnitine together account for at least 90 wt % of a dosage unit of the supplement.

7. The method of claim 1 wherein the dosage unit of the supplement is equal or less than 1,600 mg.

8. The method of claim 1 wherein the cognitive function is a function of working memory, a function of long term memory consolidation, an aspect of mood, a function of fluid intelligence, spatial memory, and object working memory.

9. The method of claim 1 further comprising a step of providing an interactive tool that allows at least one of validation of efficacy of the supplement and proper personal dosing of the supplement.

* * * * *